US010472313B1

(12) United States Patent
Voskresensky

(10) Patent No.: US 10,472,313 B1
(45) Date of Patent: Nov. 12, 2019

(54) PROCESS FOR SYNTHESIZING TRIFLUOROKETONES

(71) Applicant: Graphene Laboratories Inc., Ronkonkoma, NY (US)

(72) Inventor: Sergey Voskresensky, Miller Place, NY (US)

(73) Assignee: Graphene 3D Lab Inc., Ronkonkoma, NY (US)

( * ) Notice: Subject to any disclaimer, the term of this patent is extended or adjusted under 35 U.S.C. 154(b) by 0 days.

(21) Appl. No.: 16/278,156

(22) Filed: Feb. 17, 2019

Related U.S. Application Data

(60) Provisional application No. 62/631,779, filed on Feb. 18, 2018.

(51) Int. Cl.
*C07C 45/00* (2006.01)
*C07C 67/00* (2006.01)
*B01J 31/00* (2006.01)
*C07C 67/343* (2006.01)
*B01J 31/24* (2006.01)
*C07C 69/78* (2006.01)
*C07C 49/813* (2006.01)

(52) U.S. Cl.
CPC ......... *C07C 45/008* (2013.01); *B01J 31/2404* (2013.01); *C07C 67/343* (2013.01); *C07C 49/813* (2013.01); *C07C 69/78* (2013.01)

(58) Field of Classification Search
CPC ............................ C07C 45/008; C07C 67/343
See application file for complete search history.

(56) References Cited

U.S. PATENT DOCUMENTS 9,199,994 B2   12/2015   De Lombaert et al.

OTHER PUBLICATIONS

Shen. Palladium Catalyzed Coupling of Aryl Chlorides with Arylboronic Acids. Tetrahedron Letters, vol. 38, No. 32, pp. 5575-5578. (Year: 1997).*
Singh et al. Cesium Fluoride Catalyzed Trifluoromethylation of Esters, Aldehydes, and Ketones with (Trifluoromethyl) trimethylsilane . Journal of Organic Chemistry, vol. 64, pp. 2873-2876. (Year: 1999).*
Wiedermann et al, "Direct Preparation of Trifluoromethyl Ketones from Carboxylic Esters: Trifluoromethylation with (Trifluoromethyl)trimethylsilane," Angew. Chem. Int. Ed. 1998, 37, No. 6, pp. 820-21.

* cited by examiner

*Primary Examiner* — Sikarl A Witherspoon
(74) *Attorney, Agent, or Firm* — Mark Malek; Widerman Malek, PL

(57) ABSTRACT

A process for synthesizing trifluoroketones, such as 1-(5-chloro[1,1'-biphenyl]-2-yl)-2,2,2-trifluoroethanone.

21 Claims, No Drawings

PROCESS FOR SYNTHESIZING TRIFLUOROKETONES

CROSS-REFERENCE TO RELATED APPLICATIONS

This application makes reference to and claims the priority benefit of the following U.S. Provisional Patent Application No. 62/631,779, filed Feb. 17, 2018. The entire disclosure and contents of the foregoing Provisional Application is hereby incorporated by reference.

FIELD OF THE INVENTION

The present invention broadly relates to a process for synthesizing a trifluoroketone(s), such as 1-(5-chloro[1,1'-biphenyl]-2-yl)-2,2,2-trifluoroethanone.

BACKGROUND

Trifluoroketones are used as precursors for synthesis of tryptophan hydroxylase (TPH)-inhibiting compounds, such as those described in U.S. Pat. No. 9,199,994 (De Lombaert et al.), issued Dec. 1, 2015. These TPH-inhibiting compounds are useful in the treatment of diseases or disorders associated with peripheral serotonin including, for example, gastrointestinal, cardiovascular, pulmonary, inflammatory, metabolic, and low bone mass diseases, as well as serotonin syndrome, and cancer.

SUMMARY

According to one broad aspect of the present invention, there is provided process for synthesizing trifluoroketone(s), the process comprising the steps of:
 (a) a Suzuki coupling between a mixture of methyl- and/or ethyl-esters of 4-chloro-2-iodobenzoic acid and phenylboronic acid to form methyl- and/or ethyl-esters of 4-chloro-2-phenylbenzoic acid; and
 (b) a catalyzed trifluoromethylation of the methyl- and/or ethyl-esters of 4-chloro-2-phenylbenzoic acid of step (a) to form the corresponding trifluoroketone(s).

DETAILED DESCRIPTION

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated otherwise.

For the purposes of the present invention, the term "Suzuki coupling" refers generally to a coupling reaction between a boronic acid and an organohalide which may be catalyzed by a palladium complex catalyst, such as palladium (0) tetrakis(triphenylphosphine) (Pd(PPh$_3$)$_4$)). With respect to embodiments of the process for synthesizing trifluoroketone(s) according to the present invention, the Suzuki coupling involves a catalyzed (e.g., by palladium triphenyl phosphorous) reaction between methyl- and/or ethyl-esters of 4-chloro-2-iodobenzoic acid and phenylboronic acid which forms the corresponding methyl- and/or ethyl-esters of 4-chloro-2-phenylbenzoic acid, wherein the phenyl substituent of the phenylboronic acid replaces the iodo group of the methyl and/or ethyl esters of 4-chloro-2-iodobenzoic acid.

For the purpose of the present invention, the term "trifluoroketone(s)" refers to a ketone (or mixture of ketones) having three fluoro substituents, such as the corresponding trifluoroketone(s) formed from the trifluoromethylation of the methyl- and/or ethyl-esters of 4-chloro-2-phenylbenzoic acid. These trifluoroketone(s) may include, for example, 1-(5-chloro[1,1'-biphenyl]-2-yl)-2,2,2-trifluoroethanone (CAS #1998068-09-9), 2,2,2-trifluoro-1-(2-bromo-4-chlorophenyl)ethanone, CAS#1033805-23-0; 2,2,2-trifluoro-1-(4-chloro-2-iodophenyl)ethanone, CAS#1823918-64-4, etc.

For the purpose of the present invention, the term "methyl- and/or ethyl-esters" refers to a compound, composition, etc., which may be the methyl ester, the ethyl ester, or a mixture of methyl and ethyl esters.

For the purposes of the present invention, the term "phenyl" refers to a phenyl group which may be unsubstituted, as well as a phenyl group which may have one or more substituents which may include halo (e.g., chloro, bromo, fluoro, etc.), $C_1$ to $C_4$ alkyl (e.g., methyl, ethyl, etc.), etc.

For the purposes of the present invention, the term "trifluoromethylation" refers to a reaction where the methoxy and/or ethoxy substituent of the ester group is replaced by a trifluoromethyl group. Suitable agents for carrying out trifluoromethylation may include trifluoromethyltrimethylsilane, etc.

For the purposes of the present invention, the term "catalyzed trifluoromethylation" refers to a trifluoromethylation reaction which is carried out in the presence of a trifluoromethylation catalyst. Suitable trifluoromethylation catalysts may include, for example, cesium fluoride (CsF), quaternary ammonium fluorides (e.g., tetrabutylammonium fluoride), etc.

For the purposes of the present invention, the term "liquid" refers to a non-gaseous fluid composition, compound, substance, material, etc., which may be readily flowable at the temperature of use (e.g., room temperature) with little or no tendency to disperse and with a relatively high compressibility.

For the purposes of the present invention, the term "solid" refers to non-volatile, non-liquid components, compounds, materials, etc., which may be in the form of, for example, particulates, particles, powders, etc.

For the purposes of the present invention, the term "room temperature" refers to refers to the commonly accepted meaning of room temperature, i.e., an ambient temperature of from about 20° to about 25° C.

For the purposes of the present invention, the term "comprising" means various compositions, compounds, components, elements, steps, etc., may be conjointly employed in embodiments of the present invention. Accordingly, the term "comprising" encompasses the more restrictive terms "consisting essentially of" and "consisting of."

For the purposes of the present invention, the terms "a" and "an" and similar phrases are to be interpreted as "at least one" and "one or more." References to "an" embodiment in this disclosure are not necessarily to the same embodiment.

For the purposes of the present invention, the term "and/or" means that one or more of the various compositions, compounds, components, elements, steps, etc., may be employed in embodiments of the present invention.

Unless otherwise specified, all percentages given herein are by weight.

DESCRIPTION

Embodiments of the present invention are directed to a process for synthesizing trifluoroketone(s), such as 1-(5- chloro[1,1'-biphenyl]-2-yl)-2,2,2-trifluoroethanone, including the trifluoroketones disclosed in U.S. Pat. No. 9,199,994 (De Lombaert et al.), issued Dec. 1, 2015, the entire disclosure and contents of which are herein incorporated by reference. De Lombaert et al. suggests the following synthetic route to obtain these trifluoroketones:

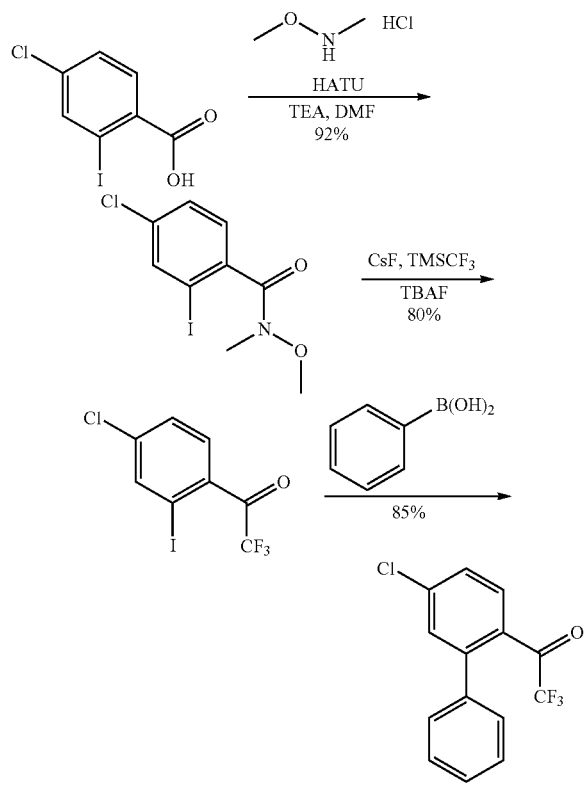

The De Lombaert et al. synthetic route shown above may have substantial drawbacks that may hinder its utilization for manufacturing of tryptophan hydroxylase (TPH)-inhibiting compounds. First, because the Suzuki coupling step in the above synthetic route suggested by De Lombaert et al. is utilized as a final step, that may cause the formation of by-products comprising derivatives of the trifluoroketone which may make final product purification cumbersome. Also, scaling up the above synthetic route suggested by De Lombaert et al. may be difficult to achieve because the set of reagents required may be expensive and the purification of the final product may be difficult to carry out.

By contrast, embodiments of the present invention provide an efficient, two-step process for synthesizing trifluoroketone(s), such as 1-(5-chloro[1,1'-biphenyl]-2-yl)-2,2,2-trifluoroethanone: (a) a Suzuki coupling between a mixture of methyl- and/or ethyl-esters of 4-chloro-2-iodobenzoic acid and phenylboronic acid to form the corresponding methyl- and/or ethyl-esters of 4-chloro-2-phenylbenzoic acid; and (b) a catalyzed trifluoromethylation of the methyl- and/or ethyl-esters of 4-chloro-2-phenylbenzoic acid with, for example, trifluoromethyltrimethylsilane (TMSCF$_3$) to form the corresponding trifluoroketone(s), such as 1-(5-chloro[1,1'-biphenyl]-2-yl)-2,2,2-trifluoroethanone, by using, for example, trifluoromethyltrimethylsilane, as the trifluoromethylation agent, and, for example, cesium fluoride as the trifluoromethylation catalyst. Embodiments of the process of the present invention may be more economical, do not require using hazardous reagents such as 1-[bis(dimethylamino)methylene]-1H-1,2,3-triazolo[4,5-b]pyridinium 3-oxid hexafluorophosphate (HATU), triethylamine, etc. The resulting products obtained by embodiments of the process of the present invention may also not be as contaminated with derivatives of the trifluoroketone(s). Any impurities formed in the resulting products according to embodiments of this process may be of low molecular mass and may be more easily removed by a simple recrystallization step.

In particular, embodiments of the process of the present invention permits industrial scale manufacturing of trifluoroketone(s), such as 1-(5-chloro[1,1'-biphenyl]-2-yl)-2,2,2-trifluoroethanone. The benefits of using embodiments of the process of the present invention for industrial manufacture of such trifluoroketone(s) may include: (1) higher reproducibility of the resulting products; and (2) using lower amounts of organic solvents (e.g., compared to the De Lombaert et al. synthetic route), and thus making embodiments of this process more ecologically friendly, as the solvents used in the work-up and the purification steps may be recyclable.

In step (a) of the process of the present invention, the methyl- and/or ethyl-esters of 4-chloro-2-iodobenzoic acid used may be the single (pure) methyl or ethyl ester, or may be a mixture of the methyl and ethyl esters in any suitable weight ratio. Mixtures of the methyl and ethyl esters have been found to provide better synthesis results and operational convenience. When mixtures of methyl esters and ethyl esters are used, the weight ratio of methyl esters to ethyl esters may be in the range of, for example, from about 4:1 to about 15:1, such as from about 7:1 to about 12:1. The methyl- and/or ethyl-esters of 4-chloro-2-iodobenzoic acid used in step (a) may be prepared, for example, by an acid (e.g., sulfuric acid) catalyzed reaction of 4-chloro-2-iodobenzoic acid with a mixture of methyl alcohol (methanol) and ethyl alcohol (ethanol). One such embodiment according to the process of the present invention for preparing these methyl- and/or ethyl-esters of 4-chloro-2-iodobenzoic acid for step (a) may be carried out as follows: The 4-chloro-2-iodobenzoic acid (143.0 kg) is charged to a 400 L jacked reactor followed by 81 kg of methyl alcohol and 14 kg of ethyl alcohol. To the resulting solution is added 29.6 kg of concentrated sulfuric acid to keep the batch temperature below 45° C. The batch temperature is adjusted to 65° C. and the resulting mixture is stirred at the same temperature for 2 days. After stirring for 2 days, the batch temperature of the resulting mixture is decreased to 15° C. with 190 kg of hexane being added followed by 68 kg of distilled water. The batch temperature is adjusted to 25° C. and the resulting mixture is then stirred for 10 min. After the resulting mixture has separated into organic and aqueous layers, the bottom aqueous layer is removed and discarded. The remaining organic layer is washed with 15 kg of 3M hydrochloric acid and then agitated for 20 minutes. After agitation and separation into organic and aqueous layers, the bottom aqueous layer is removed and discarded. The remaining organic layer is then washed twice with 70 kg of 1-2% aqueous NaOH. After the resulting mixture has separated into organic and, aqueous layers, the bottom aqueous layer is removed and discarded. At this point, the pH of the removed aqueous layer is measured to see if it is 10 or greater. If the pH is below 10, the remaining organic layer is additionally washed with 20 of 1-2% NaOH solution. Afterwards, the remaining organic layer is washed with 139 kg of 1-2% aqueous sodium sulfite. After the resulting mixture has separated into organic and aqueous layers, the bottom aqueous layer is removed and discarded. The hexane solvent is than removed from the remaining organic layer under reduced pressure at 40° C. to provide a 9:1 weight ratio mixture of methyl 4-chloro-2-iodobenzoate and ethyl 4-chloro-2-iodobenzoate as an oil, which may slowly crystallize at ambient temperature. The yield range is 90-100%.

In embodiments of the process of the present invention, the mixture of step (a) may comprise a weight ratio of methyl- and/or ethyl-esters of 4-chloro-2-iodobenzoic acid to phenylboronic acid in the range of, for example, from about 1:1 to about 5:1, such as from about 1:1 to about 1.5:1. In an embodiment of the process of the present invention for preparing, for example, 1-(5-chloro[1,1'-biphenyl]-2-yl)-2,2,2-trifluoroethanone, step (a) (i.e., the Suzuki coupling between the mixture of the methyl- and/or ethyl-esters of the 4-chloro-2-iodobenzoic acid and phenylboronic acid) uses a 16.3 kg load of starting esters in a 100 L reactor which is illustrated as follows:

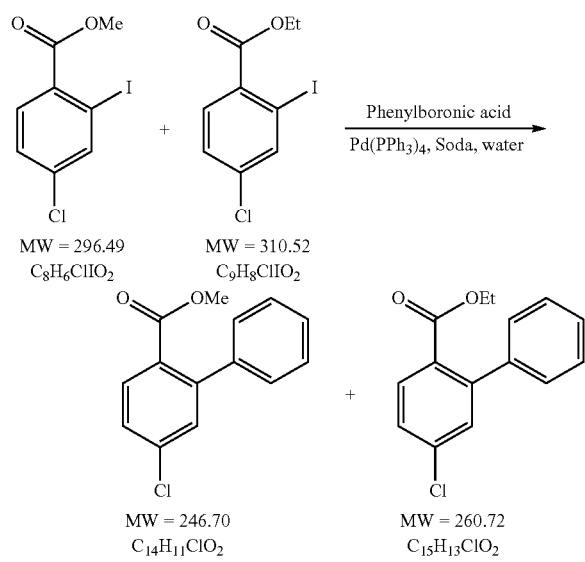

The Suzuki coupling reaction shown above may be carried out under a nitrogen atmosphere. Water may be degassed (e.g., by bubbling the nitrogen through the reaction mixture with stirring) for at least 12 hours prior to the reaction. The reaction temperature may be in the range of from about 55° to about 100° C., for example, from about 75° to about 98° C., such as from 90°–95° C., although the reaction proceeds slower at lower reaction temperatures (e.g., as low as 80° C.). The reaction vessel may be equipped with a concentrator condenser (wherein condensate drains through the side tube) so as to remove the low boiling contents from the reaction+low volatile side products (like biphenyl and methyl 4-chlorobenzoate). Sodium bicarbonate (soda) may be added portion-wise as the reaction progresses, with a final concentration of the sodium bicarbonate not exceeding about 5%. Portion-wise addition of the phenylboronic acid avoids or minimizes partial decomposition under these reaction conditions, and may also reduce the amount of the phenylboronic acid required. The palladium complex catalyst (e.g., palladium (0) tetrakis(triphenylphosphine) (Pd(PPh$_3$)$_4$)) is desirably added portion-wise during the reaction together with sodium bicarbonate. The palladium complex catalyst may added in, for example, an amount of from about 0.0001 to about 100 mol %, such as from about 0.002 to about 0.01 mol %. One of the benefits of the Suzuki coupling reaction according embodiments of the process of the present invention is minimizing the amount expensive palladium complex catalyst that are required.

In one embodiment of step (a) of this process illustrated above, a 100 L glass reactor equipped with 5-necked lid (mechanical stirrer, and 2 condensers using a digital temperature controller and one side neck designed for the powder addition) is charged with 44 L of degassed warm water which is heated to 60° C. After charging with the degassed water, 4009 g (1 equivalent) of the phenylboronic acid is added portion-wise within 20 min at 55°–60° C., followed by 1600 g of the sodium bicarbonate (added in one portion). After the addition of sodium bicarbonate, the methyl- and ethyl-esters of 4-chloro-2-iodobenzoic acid (16.3 kg) are added, followed by 400 ml of dimethylformamide (DMF) and 300 mg of the palladium complex catalyst (i.e., palladium (0) tetrakis(triphenylphosphine) (Pd(PPh$_3$)$_4$)) with the resulting mixture being gradually heated to 88° C. within 1 hour. Another 100 mg portion of the palladium complex catalyst is then added, and the resulting mixture is stirred at 88°-90° C. for an additional 1.5 hours. The reaction is monitored by gas chromatography/mass spectrometry (GC/MS). All further substeps (1 through 10) in this reaction during step (a) are described in the Table below:

| Step # | Reaction conversion (by GC/MS) | Reagent(s) added after QC | Temperature |
|---|---|---|---|
| 1 | 4% | | 95° C. |
| 2 | 9.3% | | 95° C. |
| 3 | 17.5% | 800 g sodium bicarbonate, 200 mg Pd (0) | 95° C. |
| 4 | 41% | 1300 g sodium bicarbonate, 2500 g phenylboronic acid 150 mg Pd (0) | 95° C. |
| 5 | 59% | 600 g sodium bicarbonate, 150 mg Pd (0) | 95° C. |
| 6 | 75% | 600 g sodium bicarbonate, 400 mg Pd (0) | 95° C. |
| 7 | 86% | 300 g sodium bicarbonate, 400 g phenylboronic acid 90 g phenylboronic acid, 200 g sodium bicarbonate | 95° C. |
| 8 | 98% | | 98° C. |
| 9 | 99.5% | 30 g phenylboronic acid, 200 g sodium bicarbonate, 100 mg Pd (0) | 98° C. |
| 10 | 100% | | |

The resulting mixture from this reaction is cooled to room temperature and 20 L of the hexane is added with stirring. The resulting mixture is stirred for 10 min and then stirring is terminated. About 50% of the bottom aqueous layer is transferred into a 72 L separatory funnel by vacuum suction using HDPE tubing. The resulting aqueous layer is extracted with 10 L of hexane with the water being drained from the funnel. After draining of the water, the residual contents of the reactor are transferred into the 72 L separatory funnel by vacuum suction using HDPE tubing. The combined hexane layers are washed sequentially as follows: (1) with 2% sodium hydroxide (15 L); (2) with 2-3% sodium sulfite (10 L); and (3) with warm water (15 L).

After washing, the resulting hexane solution is passed through 3 columns filled with silica gel (600 g in each column) with anhydrous sodium sulfate on top (400 g). After the hexane solution is passed through the columns, these columns are washed again with pure hexane (3 L per column), with the sodium sulfate and thin black layer of silica gel formed on the top of the column being replaced with fresh sodium sulfate and silica gel. The hexane solvent is evaporated under reduced pressure to provide the resulting mixture of the methyl and ethyl esters. The resulting mixture is then dried under high vacuum for 2 days. Actual yield: 13550 g. (99%). Theoretical yield: 1354.2 g.

The above described step (a) may be scaled up as follows:

1. Use of larger chemical reactors equipped with an adequate heating system. Thus, the use of a 200 L double jacketed glass reactor allows for an increase in the amount of the starting materials by a factor of 2. Accordingly, the use of a 500 L stainless steel reactor allows for an increase the amount of the starting reactants by the factor of 5.

2. By decreasing the original amount of water used in the synthesis. The amount of water used in the reaction is a major contribution to the overall volume. Therefore, decreasing the water volume allows an increase in the amount of the starting materials. Thus, decreasing the water volume by 30% allows for an increase in amount the starting materials by 25%. In this case, the amounts of sodium bicarbonate added during the reaction may need to be pro-rated accordingly so that sodium bicarbonate concentration does not exceed 5%.

One scaled up embodiment of step (a) of the process of the present invention may be carried out as follows: Phenylboronic acid (42 kg), sodium bicarbonate (9.1 kg), and palladium (0) tetrakis(triphenylphosphine) catalyst (27.1 g) are charged into a 600 L jacketed reactor with stirring. Then, degassed deionized water (227 kg) is added, followed by a 9:1 weight ratio mixture of methyl 4-chloro-2-iodobenzoate and ethyl 4-chloro-2-iodobenzoate (93 kg), dimethylformamide (3.8 kg), and toluene (23 kg) at 30° C. The resulting mixture is then heated to 75° C. Progress of the reaction is monitored by measuring the pH of the mixture. When the reaction temperature reaches 75° C., the pH of the mixture should be below 6. Then, a second portion of sodium bicarbonate (9.1 kg) is added portion-wise. The resulting mixture is stirred at 75° C. until the pH of the reaction mixture reaches a value of 6.5-7 (2-4 hours). Then a third charge of sodium bicarbonate (9.1 kg) is added and the resulting mixture is stirred until the pH value of the reaction mixture reaches below 7.5 (2-4 hours). Finally, additional palladium (0) tetrakis(triphenylphosphine) catalyst (7.2 g) is added followed by sodium bicarbonate (6.7 kg). The reaction mixture is then stirred at 75° C. until complete conversion of the starting materials (as measured by GC/MS or GC, 2-6 hours). The reaction mixture is then cooled to a temperature of 25° C. and hexane (63 kg) is added with the resulting mixture being stirred for 10 minutes. After the resulting mixture has separated into organic and aqueous layers, the aqueous layer is removed and discarded. The organic layer is washed twice with 1-3% aqueous NaOH (58 kg). After the resulting mixture has again separated into organic and aqueous layers, the aqueous layer is removed and discarded. The remaining organic layer is then washed with 1-2% aqueous sodium sulfite (57 kg). After the resulting mixture has again separated into organic and aqueous layers, the aqueous layer is removed and discarded. The remaining organic layer is then dried over sodium sulfate (4 kg) and passed through a column filled with silica gel (6 kg). The silica gel is washed with 30 L of pure hexane and the resulting combined organic layers are concentrated under reduced pressure at 50° C. to remove the hexane solvent. The resulting mixture of the methyl and ethyl esters (methyl 4-chloro-2-phenylbenzoate and ethyl 4-chloro-2-phenylbenzoate in a 9:1 weight ratio) is obtained as an oil. The yield range is 90-99%.

In an embodiment of the process of the present invention for preparing 1-(5-chloro[1,1'-biphenyl]-2-yl)-2,2,2-trifluoroethanone, step (b) (i. (i.e., a catalyzed trifluoromethylation of the methyl- and ethyl-esters of the 4-chloro-2-phenylbenzoic acid to form the corresponding trifluoroethanone), an 18 kg load of the starting methyl- and/or ethyl-esters may be used in a 50 L reactor, as illustrated as follows:

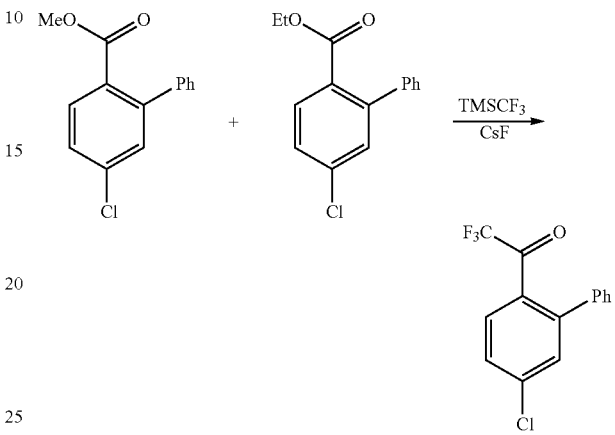

The catalyzed trifluoromethylation reaction shown above for step (b) may use a weight ratio of methyl- and ethyl-esters of 4-chloro-2-phenylbenzoic acid to trifluoromethyltrimethylsilane (TMSCF$_3$) in the range of, for example, from about 1:1 to about 1.5:1, such as from about 1.1:1 to about 1.3:1, and may be carried out under a nitrogen atmosphere. The ratio between the solvent (in ml) and starting esters (in g) may be kept, for example, at 1:5. The cesium fluoride is dried at 140° C. for 24 hours prior to use and may be used in an amount of, for example, from about 8 to about 20 weight %, such as from about 9.2 to about 10.2 weight %. The addition of trifluoromethyltrimethylsilane is desirably carefully controlled by constant monitoring of the reaction temperature. Step (b) may be carried out, for example, at a temperature in the range of from about −20° to about 60° C., such as from about 0° to about 20° C.

One embodiment of step (b) of this process illustrated above may be carried out as follows: The 50 L glass reactor is equipped with a 5-necked lid (for receiving a mechanical stirrer, condenser, addition funnel, temperature probe connected to the digital temperature reader, and one side neck designed for powder addition) and charged with a mixture of the methyl- and ethyl-esters of 4-chloro-2-phenylbenzoic acid, followed by the addition of dry, finely ground cesium fluoride (1.66 kg). This mixture is stirred at ambient conditions for 45 min, and 3.6 L of the anhydrous tetrahydrofuran is then added. The resulting mixture is cooled down to 5° C. using an ice-water bath. To the resulting well-stirred solution is added 0.15 equivalents of trifluoromethyltrimethylsilane dropwise within 20 minutes. The following color changes of the reaction mixture are observed: orange-amber-green. By the end of this addition, an exothermic reaction begins, and the temperature of the reaction rises to 11° C. At this point, the addition of the trifluoromethyltrimethylsilane is terminated and the reaction mixture is stirred for 1 hour until the temperature inside the reactor decreases to 6° C. The rest of the trifluoromethyltrimethylsilane is then added portion-wise to the reaction mixture so as to keep the temperature of the reaction mixture within the range of 7°–12° C. The progress of the reaction is monitored using a GC/MS instrument. After about 90% of the trifluoromethyltrimethylsilane is added, 800 ml of anhydrous tetrahydrofuran is then added to avoid product crystallization. After trifluoromethyltrimethylsilane addition is completed, the reaction mixture is stirred for 10 hours at 12°–15° C. Three liters of the methyl alcohol is then carefully added to make sure that no exothermic reaction is occurring, followed by portion-wise addition of potassium carbonate (4×50 g). The resulting reaction mixture is slowly (within 3 hours) heated to 30° C. and stirred at this temperature for 4 additional hours. At this point, the reaction mixture is analyzed by GC/MS to determine completion of the deprotection reaction. After GC/MS analysis, the reaction mixture is cooled to 20° C. and 2.5 L of 37% hydrochloric acid is added portion-wise with sufficient stirring within 2 hours. Finally, the reaction mixture is heated within 2 hours up to 55° C. and stirred at this temperature for an additional 24 hours.

The reaction mixture is then cooled to 20° C. and 3 L of deionized water is added with stirring. The contents of the reactor are then transferred to a 72 L separatory funnel (vacuum transfer using HDPE tubing), with an extra 5 L of deionized water being added followed by 10 L of hexane. The resulting mixture is stirred well, and the organic (top) layer is removed by vacuum suction. The remaining aqueous layer is diluted with deionized water (10 L) and extracted one more time with 10 L of hexane. The resulting aqueous layer is then transferred to a drum for proper disposal.

The organic layers of these two separations are combined in the 72 L separatory funnel, with an additional 10 L of the hexane being added, and the resulting solution washed twice with 15 L (each wash) of deionized water. The resulting hexane solution is dried using 600 g of anhydrous sodium sulfate.

The resulting dried hexane solution is passed through 3 columns filled with the silica gel (400 g in each). After that, each column is washed with pure hexane (3 L per column). Hexane is removed from the resulting solution under reduced pressure (e.g., using rotary evaporators). The resulting evaporated residue is re-dissolved with stirring in hexane (ACS grade, 650 ml of the hexane per 1 kg of the crude material) using a 50 L reactor and the resulting mixture is then cooled within 2 hours with the stirring to −5° C. During this cooling, the desired product precipitates from the reaction mixture. The desired product is filtered off and washed with cold hexane at 5° C. At this point the product quality is analyzed using GC/MS. After that, this crystallization procedure is repeated one more time. After passing the QC routing test (by GC/MS analysis), the final product is dried in vacuum ovens for 2 days. Actual yield: 18577 g (91%). Theoretical yield: 20414 g.

The above described step (b) may be scaled up as follows: to a hundred kilogram scale by using high capacity chemical reactors (vessels). These reactors may be equipped with appropriate cooling systems for optimal performance. Thus, the use of a 200 L double jacketed glass reactor connected to an external cooling circulator allows for an increase in the amount of the starting materials by the factor of 4.

One scaled up embodiment of step (b) of the process of the present invention may be carried out as follows: To a stirred mixture of methyl 4-chloro-2-phenylbenzoate and ethyl 4-chloro-2-phenylbenzoate (60.0 kg) is added anhydrous cesium fluoride (6.1 kg) under the nitrogen atmosphere in 400 L reactor at 20° C. The resulting mixture is stirred for 20 min and then anhydrous tetrahydrofuran (10.7 kg) is added. The resulting mixture is cooled to 7° C. and then trifluoromethyltrimethylsilane (4.1 kg) is added dropwise within 1 hour while maintaining the temperature at 7° C. The reaction is continued with stirring until an exothermic increase in temperature occurs (e.g., an increase of 2°–7° C.). After the end of the exothermic increase in temperature, more trifluoromethyltrimethylsilane (18.6 kg) is added portion-wise over 2 hours while maintaining the temperature at 7° C. The reaction mixture is then stirred for 20 min with the temperature of the reaction mixture being increased to 12° C. The reaction mixture is stirred at 12° C. for 10 min, and then another portion of trifluoromethyltrimethylsilane (18.6 kg) is added while maintaining the temperature at 12° C. The reaction mixture is stirred at 12° C. until reaction completion is achieved (e.g., a conversion of >99.5% to the corresponding trifluoroketones as measured by by GC or GC/MS, typically in 2-8 hours). The reaction mixture is then cooled down to 5° C. and 12.0 kg of ethyl alcohol was added portion-wise. The reaction mixture is then stirred for 20 min, followed by the portion-wise addition of potassium carbonate (0.85 kg). The resulting mixture ss stirred for an additional 15 hours at 15° C. The reaction temperature is then adjusted to 20°–25° C., followed by the addition of deionized water (33 kg of) and then hexane (88 kg). The resulting mixture is stirred for 10 minutes. After the resulting mixture separates into aqueous and organic layers, the aqueous layer is removed and discarded. To the remaining organic layer is slowly added 31% hydrochloric acid (7.7 kg) with stirring while maintaining the temperature below 25° C. The resulting mixture is stirred for 1 hour at room temperature and then for an additional 5 hours at 45° C. The temperature of the resulting mixture is cooled to 20° C., followed by adding deionized water (33 kg of) and then more hexane (44 kg) with stirring for 10 min. After the resulting mixture separates into aqueous and organic layers, the aqueous layer is removed and discarded. The organic layer is washed with 33 kg of 1-2% aqueous sodium sulfite. After the resulting mixture again separates into aqueous and organic layers, the aqueous layer is removed and discarded. An additional 22 kg of hexane is added to the remaining organic layer which is then washed twice with 54 kg of deionized water. The resulting organic layer that separates out is isolated and dried over sodium sulfate (5 kg). The hexane solvent is removed from resulting organic layer under reduced pressure, and an additional 73 kg of the hexane is then added. The resulting solution is cooled to −15° C. and stirred at this temperature for 2 hours. The resulting crystals that form are filtered off, washed twice with 11 kg of cold hexane (−15° C.) and then dried to provide a white solid as the final product. The yield range is 70-90%.

All documents, patents, journal articles and other materials cited in the present application are hereby incorporated by reference.

Although the present invention has been fully described in conjunction with several embodiments thereof, it is to be understood that various changes and modifications may be apparent to those skilled in the art. Such changes and modifications are to be understood as included within the scope of the present invention as defined by the appended claims, unless they depart therefrom.

In addition, the purpose of the Abstract of the Disclosure in this application is to enable the U.S. Patent and Trademark Office, as well as the public generally, including any scientists, engineers and practitioners in the art who may not be familiar with patent or other legal terms or phraseology to determine the what the technical disclosure of the application describes. Accordingly, while the Abstract of the Disclosure may be used to provide enablement for the following claims, it is not intended to be limiting as to the scope of those claims in any way.

Finally, it is the applicant's intent that only claims which include the express language "means for" or "step for" be interpreted under 35 U.S.C. § 112, paragraph 6. Accordingly, claims that do not expressly include the phrase "means for" or "step for" are not to be interpreted as being within the purview of 35 U.S.C. § 112, paragraph 6, or to be construed as being subject to any case law interpreting the meaning of these phrases.

What is claimed is:

1. A process for synthesizing trifluoroketone(s), the process comprising the steps of:
    (a) a Suzuki coupling between a mixture of methyl- and/or ethyl-esters of 4-chloro-2-iodobenzoic acid and phenylboronic acid to form methyl- and/or ethyl-esters of 4-chloro-2-phenylbenzoic acid; and
    (b) a catalyzed trifluoromethylation of the methyl- and/or ethyl-esters of the 4-chloro-2-phenylbenzoic acid of step (a) to form the corresponding trifluoroketone(s).

2. The process of claim 1, wherein the trifluoroketone(s) formed in step (b) comprise 1-(5-chloro[1,1-biphenyl]-2-yl)-2,2,2-trifluoroethanone, 2,2,2-trifluoro-1-(2-bromo-4-chlorophenyl)ethanone, or 2,2,2-trifluoro-1-(4-chloro-2-iodophenyl)ethanone.

3. The process of claim 2, wherein the phenylboronic acid of step (a) comprises phenylboronic acid having an unsubstituted phenyl group and wherein the trifluoroketone formed in step (b) comprises 1-(5-chloro[1,1'-biphenyl]-2-yl)-2,2,2-trifluoroethanone.

4. The process of claim 1, wherein step (a) is carried out at a temperature in the range of from about 55° to about 100° C.

5. The process of claim 4, wherein step (a) is carried out at a temperature in the range of from about 75° to about 98° C.

6. The process of claim 1, wherein the mixture of step (a) comprises a weight ratio of the methyl- and/or ethyl-esters of 4-chloro-2-iodobenzoic acid to the phenylboronic acid in the range of from about 1:1 to about 5:1.

7. The process of claim 6, wherein the mixture of step (a) comprises a weight ratio of the methyl- and/or ethyl-esters of 4-chloro-2-iodobenzoic acid to the phenylboronic acid in the range of from about 1.1:1 to about 1.5:1.

8. The process of claim 1, wherein the Suzuki coupling of step (a) is carried oat with a palladium complex catalyst.

9. The process of claim 8, wherein palladium complex catalyst comprises palladium (0) tetrakis(triphenylphosphine) ($Pd(PPh_3)_4$).

10. The process of claim 7, wherein the amount of palladium (0) tetrakis(triphenylphosphine)($Pd(PPh_3)_4$)) is in in the range of from about 0.0001 to about 100 mol %.

11. The process of claim 10, wherein the amount of palladium (0) tetrakis(triphenylphosphine)($Pd(PPh_3)_4$)) is in in the range of from about 0.002 to about 0.01 mol %.

12. The process of claim 1, wherein the methyl- and/or ethyl-esters of 4-chloro-2-iodobenzoic acid of step (a) comprise a mixture of methyl and ethyl esters of 4-chloro-2-iodobenzoic acid in a weight ratio of methyl esters to ethyl esters of from about 4:1:to about 15:1.

13. The process of claim 12, wherein the weight ratio of methyl esters to ethyl esters is from about 7:1:to about 12:1.

14. The process of claim 1, wherein the trifluoromethylation of step (b) is carried out by using trifluoromethyltrimethylsilane.

15. The process of claim 14, wherein the trifluoromethylation of step (b) is carried out by using a weight ratio of methyl- and/or ethyl-esters of 4-chloro-2-phenylbenzoic acid to trifluoromethyltrimethylsilane of from about 1:1 to about 1.5:1.

16. The process of claim 15, wherein the trifluoromethylation of step (b) is carried out by using a weight ratio of methyl- and/or ethyl-esters of 4-chloro-2-phenylbenzoic acid to trifluoromethyltrimethylsilane of form about 1.1:1 to about 1.3.

17. The process of claim 14, wherein the trifluoromethylation of step (b) is carried out at a temperature in the range of from about −20° to about 60° C.

18. The process of claim 17, wherein the trifluoromethylation of step (b) is carded out at a temperature in the range of from about 0° to about 20° C.

19. The process of claim 18, wherein the trifluoromethylation of step (b) is carried out with cesium fluoride as the catalyst in an amount of from about 8 to about 20 weight %.

20. The process of claim 19, wherein the cesium fluoride is used in an amount of from about 9.2 to about 10.2 weight %.

21. The process of claim 19, wherein the trifluoromethylation of step (b) is carried out by using anhydrous tetrahydrofuran as the solvent.

* * * * *